United States Patent [19]
Goldsmith, III et al.

[11] Patent Number: 5,197,982
[45] Date of Patent: Mar. 30, 1993

[54] ADJUSTABLE PROSTHETIC DEVICE FOR VOCAL CORD AND METHOD

[76] Inventors: Manning M. Goldsmith, III, Suite 103, 4750 Waters Ave., Savannah, Ga. 31404; Bruce W. Pearson, 4500 San Pablo Rd., Jacksonville, Fla. 32225

[21] Appl. No.: 776,822

[22] Filed: Oct. 15, 1991

[51] Int. Cl.⁵ .............................. A61F 2/20; A61F 2/04
[52] U.S. Cl. ........................................ 623/9; 623/12; 623/26; 606/196
[58] Field of Search ................. 623/9, 12, 17, 11, 66, 623/26; 600/23, 24; 606/192, 196

[56] References Cited

U.S. PATENT DOCUMENTS

| | | | |
|---|---|---|---|
| 3,818,894 | 6/1974 | Wichterle et al. | 623/66 X |
| 4,198,542 | 4/1980 | Ducommun | 128/905 X |
| 4,731,083 | 3/1988 | Fischell | 623/11 |
| 4,822,333 | 4/1989 | Lavarenne | 600/30 |
| 4,932,975 | 6/1990 | Main et al. | 623/17 |

FOREIGN PATENT DOCUMENTS 1191075  11/1985  U.S.S.R. .................. 623/12

*Primary Examiner*—Randall L. Green
*Assistant Examiner*—D. Willse
*Attorney, Agent, or Firm*—Rodman & Rodman

[57] ABSTRACT

An adjustable prosthetic device for a vocal cord includes an actuator member for locating a paralyzed vocal cord in a predetermined phonation position. The device further includes a support member for supporting the actuator member in a predetermined position proximate the paralyzed vocal cord. A fluid input/withdrawal station for introducing or removing fluid from engagement with the actuator member enables the actuator member to change the location of the paralyzed vocal cord from a first predetermined phonation position to another selected position. In several embodiments of the invention the actuator member is a fluid expandable shell. In other embodiments of the invention the actuator member is a piston-expandable bellows and a movable ratchet member. The support member that supports the actuator member can be hung onto a thyroid cartilage or passed through the thyroid cartilage. The fluid input/withdrawal station can be provided adjacent the thyroid cartilage or loacted remote from the thyroid cartilage. In all embodiments of the invention the actuator member can be adjusted postoperatively without need for further surgery.

36 Claims, 7 Drawing Sheets

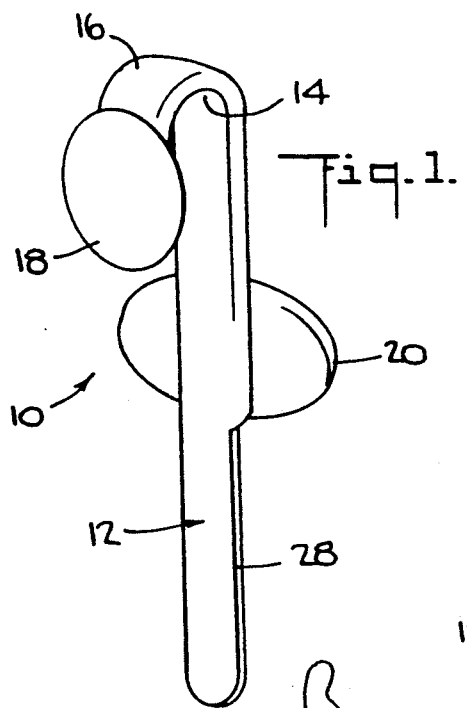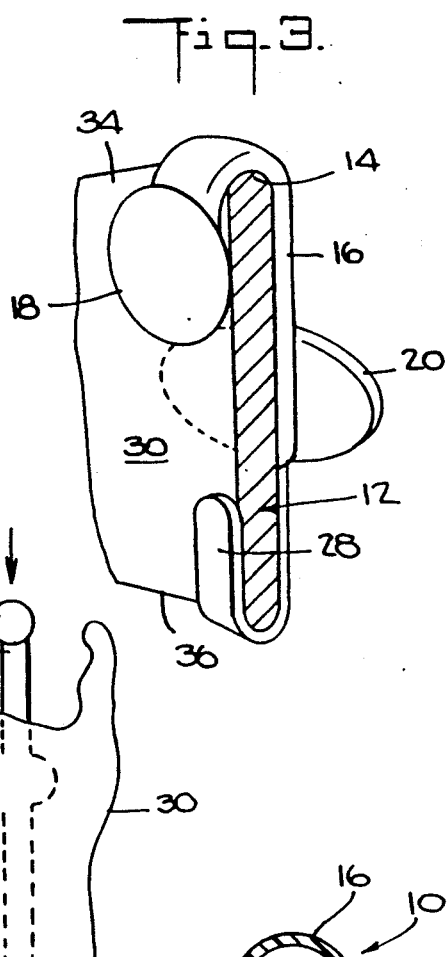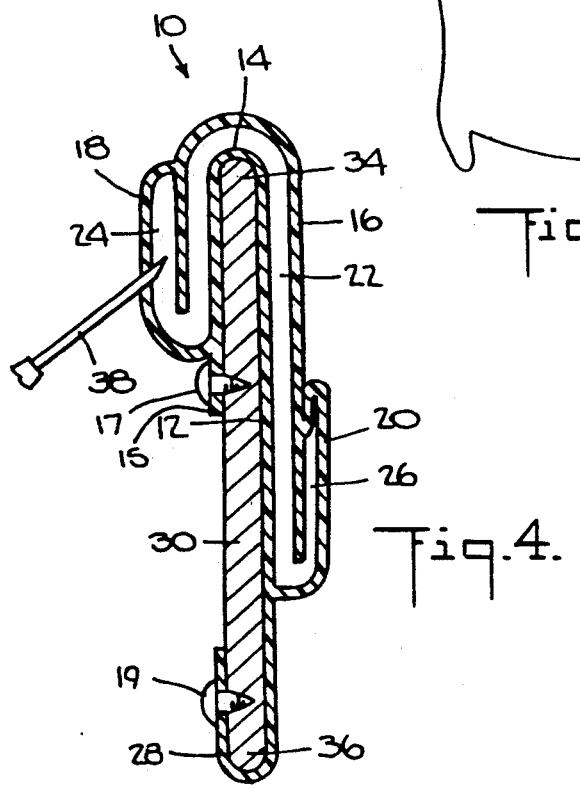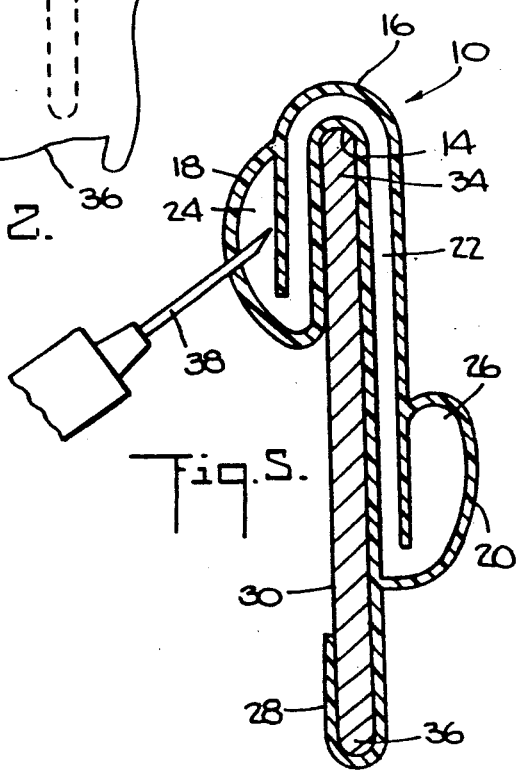

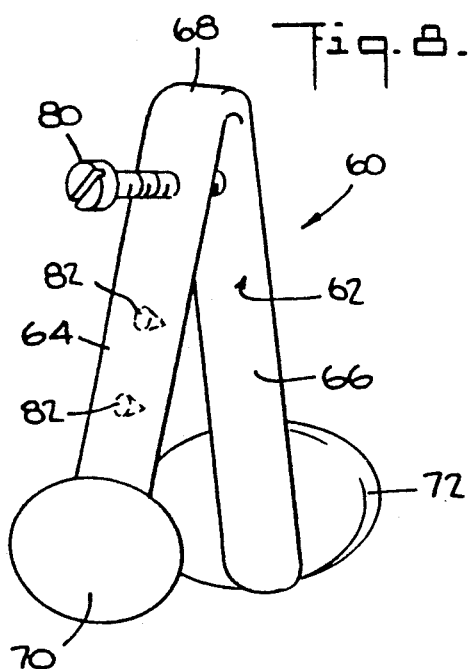
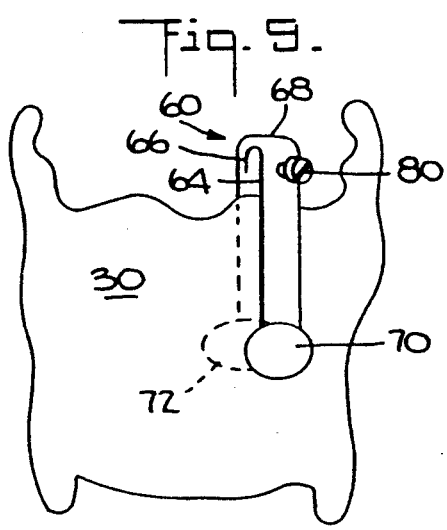
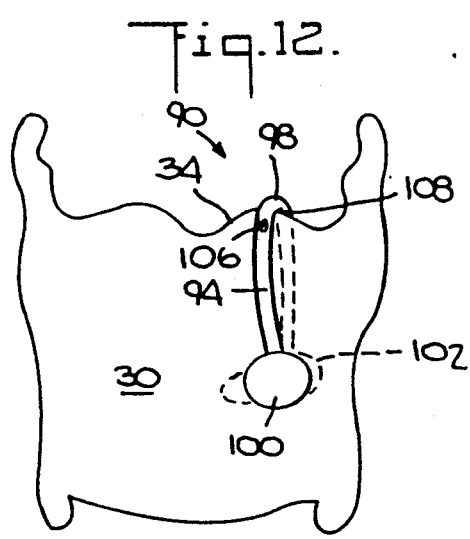
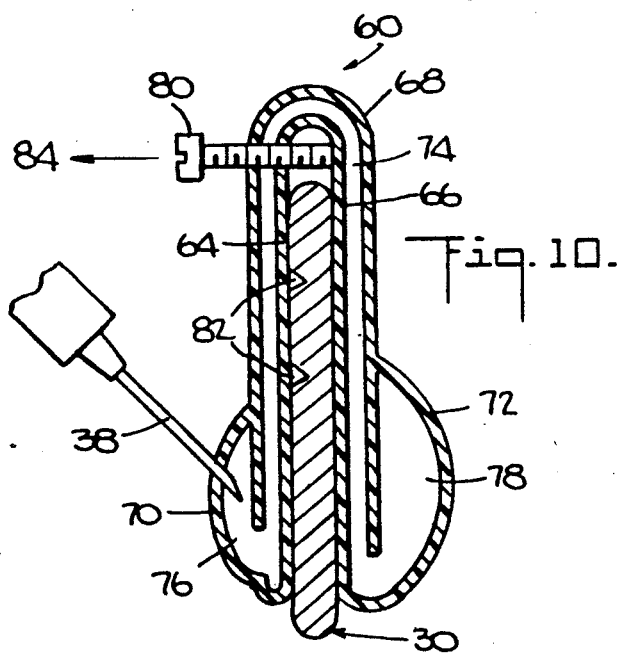
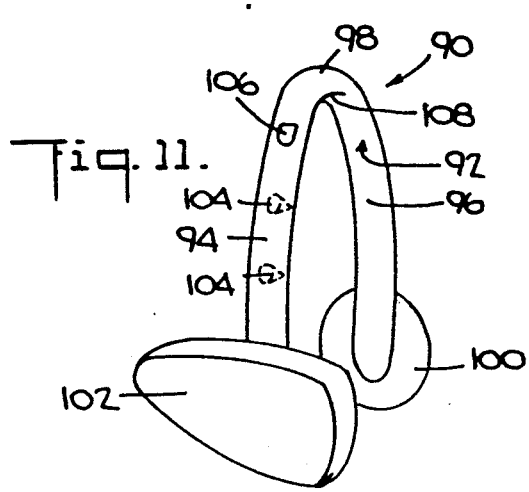
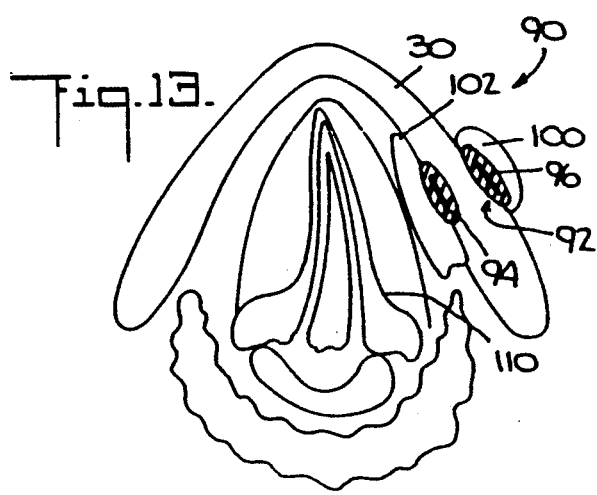

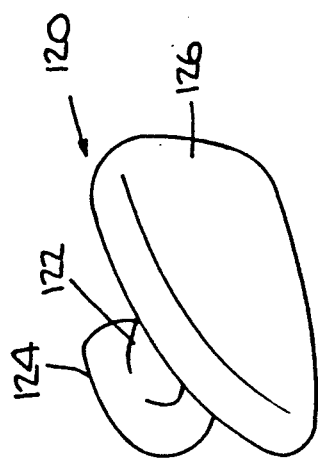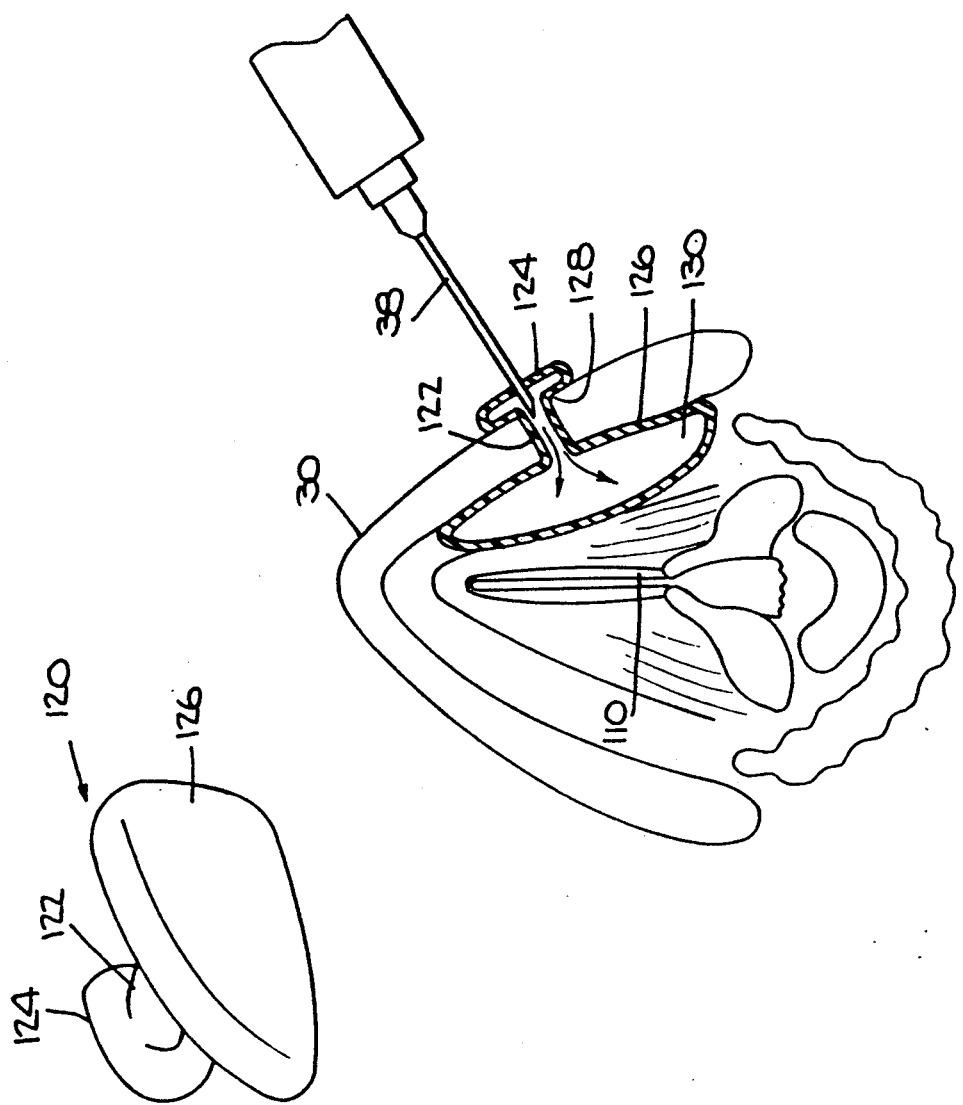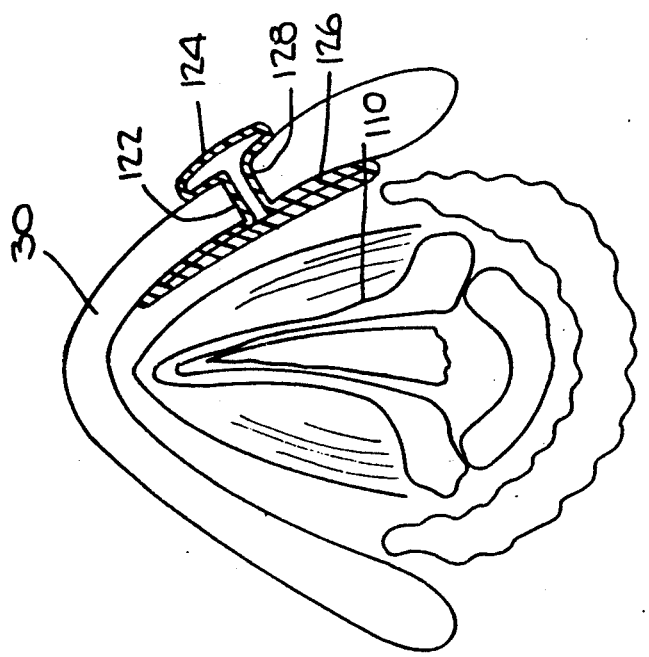
Fig. 14.
Fig. 16.
Fig. 15.

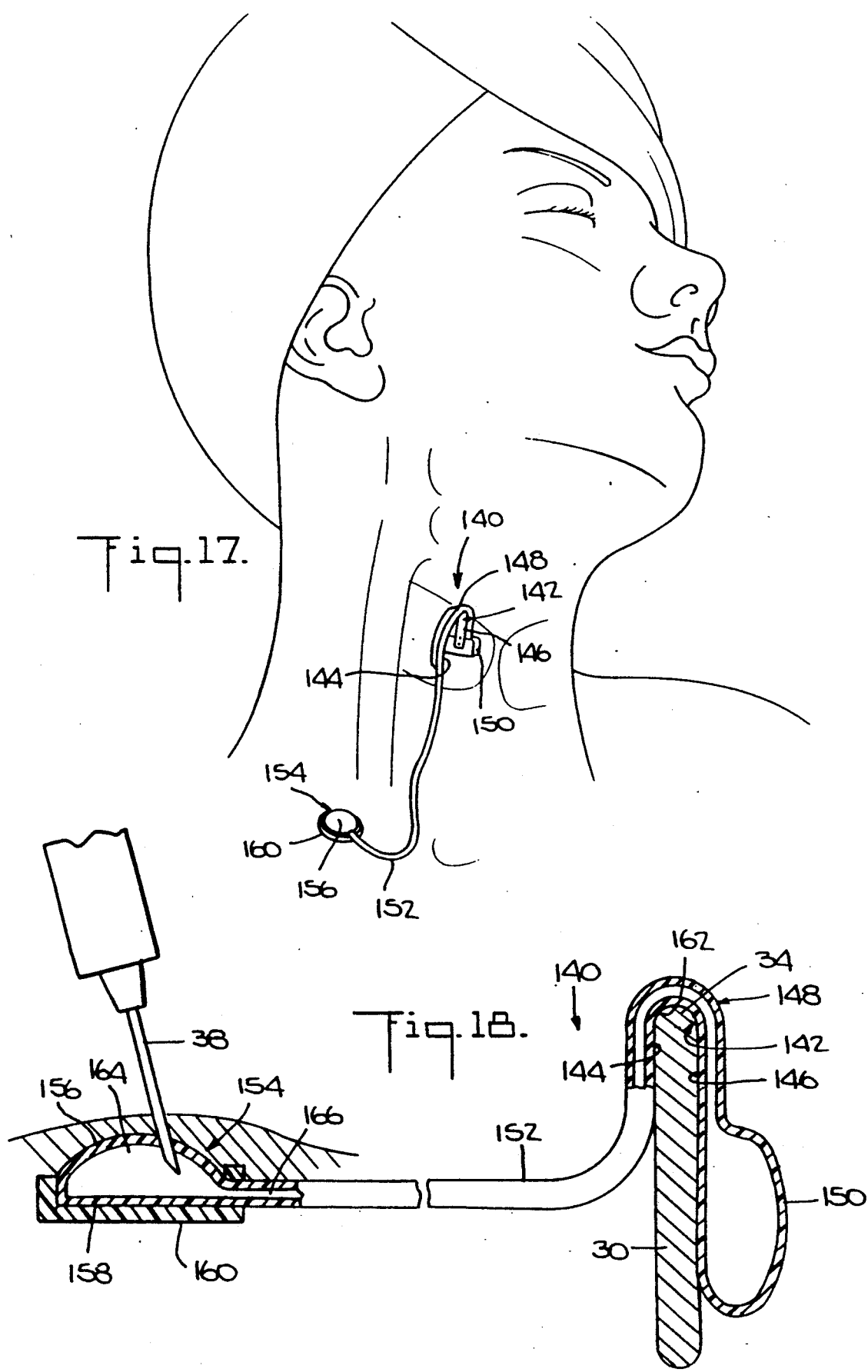

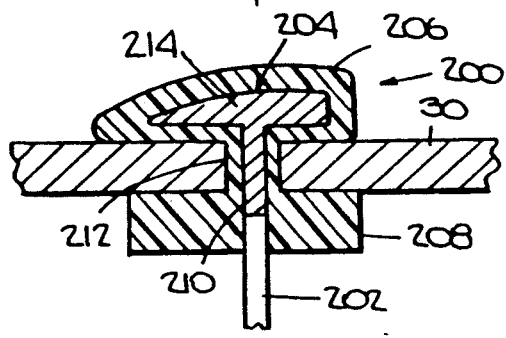
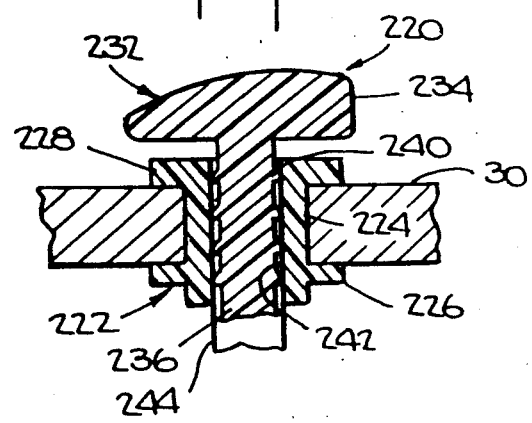
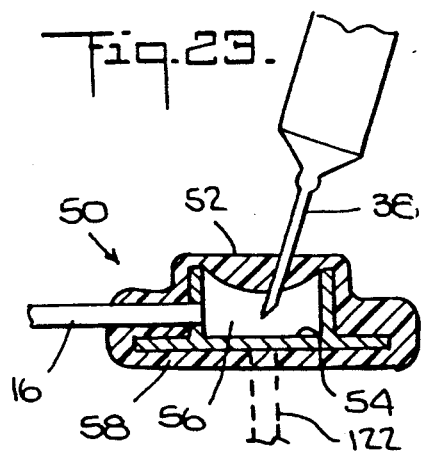
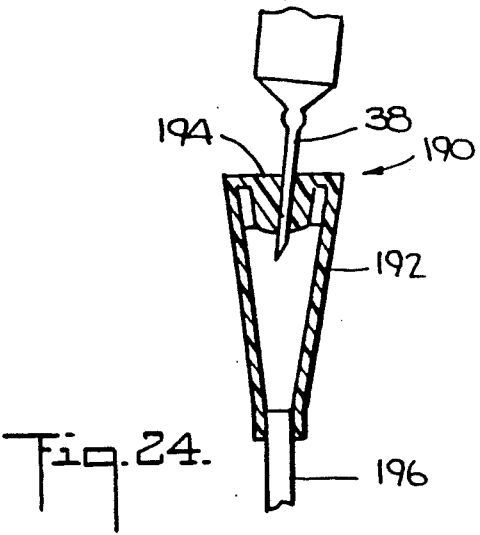
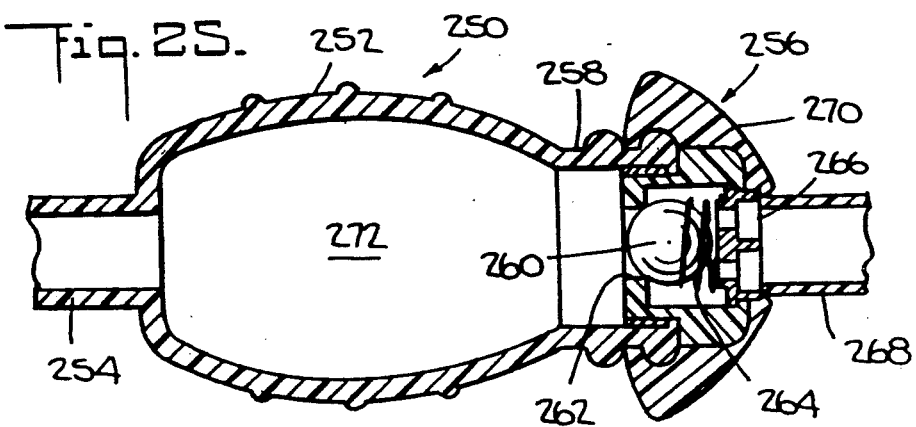

ADJUSTABLE PROSTHETIC DEVICE FOR VOCAL CORD AND METHOD

BACKGROUND OF THE INVENTION

This invention relates to treatments for vocal cord paralysis and more particularly to a prosthetic device for a vocal cord that locates a paralyzed vocal cord in a phonation position and is postoperatively adjustable to change the position of the paralyzed vocal cord.

During normal vocal cord operation the vocal cords, i.e., the glottic mucous membranes, elastic membranes, muscles, and cartilages within the larynx, are movable between a relatively closed convergent phonation position proximate the middle of the larynx, and a relatively open divergent breathing position. Thus the vocal cords normally undergo dynamic movement between their relatively closed phonation position to their relatively open breathing position to enable a speaker to breathe efficiently and noiselessly during exercise, while talking or otherwise phonating with good volume when sedentary.

If one of the vocal cords is paralyzed, it will usually recede into a slightly divergent open position resulting in reduced phonation capability.

Paralysis of a single vocal cord is thus generally treated by moving the paralyzed vocal cord to a compromise position that improves phonation (but at the expense of breathing). Since it is difficult to breathe deeply and rapidly when one vocal cord is in the fully converged phonation position and it is very difficult to speak with one vocal cord in a fully diverged breathing position, the compromise position of the paralyzed vocal cord provides less than optimum voice quality and less than optimum breathing efficiency in order that both such functions can occur. However the compromise position of a paralyzed vocal cord is usually determined empirically during surgery.

In one known treatment for vocal cord paralysis, a gel foam collagen or Teflon ® paste is injected into the paralyzed vocal cord to increase its size and thus change the vocal cord position to one which permits stronger phonation without obstructing breathing. However the injected material cannot be post-surgically adjusted or shifted to improve phonation or breathing.

In another known treatment as shown in U.S. Pat. No. 3,818,894, a water-expandable reed-like structure is implanted in a dry state into the paralyzed vocal cord. After implantation, the reed-like structure undergoes a sponge-like expansion that increases the size of the paralyzed vocal cord and changes its position to a desired phonation position that also permits breathing. However, the size of the implant again cannot be post-surgically adjusted and thus the vocal cord position obtained as a result of vocal cord expansion cannot be changed without further surgery.

If a vocal cord is only temporarily paralyzed, it is usually impractical to inject gels or install prosthetic devices into the vocal cord, especially if there is an intent at some later time to restore the vocal cord to its preoperative condition. In such instances, a paralyzed vocal cord can be temporarily repositioned by inserting a wedge-like prosthetic device between the thyroid cartilage, which surrounds the front and sides of the larynx, and the paralyzed vocal cord, much as a shim is used to adjust the position of a structure.

During installation of the wedge-like prosthetic device, a patient may be asked to phonate or speak while the surgeon adjusts the position or size of the wedge to obtain the best possible voice quality and breathing function under the circumstances. However, the surgically determined position of a paralyzed vocal cord cannot be modified without undergoing further surgery. Furthermore, due to intraoperative swelling which will later resolve, the position determined at surgery may not turn out to be the optimum position after the surgery has healed.

Any surgical or injection relocation of a paralyzed vocal cord from its receded position to a phonation position often results in tissue swelling that, in some instances, can be anticipated and allowances made. However, because the effects of swelling on the repositioning of a paralyzed vocal cord are somewhat unpredictable, it would be beneficial to make final adjustments of the repositioned paralyzed vocal cord after the swelling subsides. Scar tissue can also form in varying amounts in the vicinity of a repositioned paralyzed vocal cord to adversely affect the voice quality of a patient. Since postoperative access to the paralyzed vocal cord to make a final adjustment requires further surgery, such adjustments are not feasible.

It is thus desirable to provide a prosthetic device for a paralyzed vocal cord that can be adjusted after surgery is completed to optimize voice quality and breathing function.

OBJECTS AND SUMMARY OF THE INVENTION

Among the several objects of the invention may be noted the provision of a novel prosthetic device for a paralyzed vocal cord, a novel prosthetic device for a paralyzed vocal cord that is postoperatively adjustable, a novel prosthetic device for a paralyzed vocal cord that is postoperatively adjustable by the physician to change the position of a paralyzed vocal cord to an optimum compromise position for speaking and breathing, a novel prosthetic device for a paralyzed vocal cord having novel retaining means for supporting the device in the larynx, and a novel method for restoring and improving phonation in an individual having a paralyzed vocal cord.

Other objects and features of the invention will be in part apparent and in part pointed out hereinafter.

In accordance with the invention, the prosthetic device for a vocal cord includes a movable actuating means for locating a paralyzed vocal cord in a predetermined phonation position. The actuating means are supported by a support means proximate the paralyzed vocal cord. The prosthetic device further includes a fluid receiving station for inputting fluid to the actuating means to adjust the movement of the actuating means to change the location of the paralyzed vocal cord from a first predetermined phonation position to another selected position.

The prosthetic device is thus adjustable during surgical installation and is also adjustable post surgically after installation of the prosthetic device has been completed and direct access to the paralyzed vocal cord is not obtainable without further surgery. Post surgical adjustment of the actuating means is generally accomplished by the movement of fluid in the prosthetic device to cause a change in position of the actuating means, and a consequential change in position of the paralyzed vocal cord.

For example, in several embodiments of the invention the prosthetic device includes a tube member provided on a clip member that is joined to the thyroid cartilage. An expandable shell member is provided at one end of the tube member and a septum is provided at an opposite end of the tube member such that the chamber in the septum communicates with the chamber in the expandable shell through the tube member.

The prosthetic device is located on the thyroid cartilage such that the expandable shell is positioned proximate the paralyzed vocal cord. Infusion of fluid in the septum by a needle for example, fills the space within the septum chamber as well as the passageway in the tube and likewise fills the chamber of the expandable shell. Expansion of the shell enables the shell to move the paralyzed vocal cord from its receded and relatively divergent paralyzed position to a desired convergent phonation position.

In several embodiments of the invention the septum or actuating means is supported adjacent the thyroid cartilage, and in other embodiments of the invention the septum is implanted at a remote location away from the thyroid cartilage.

In further embodiments of the invention the support means for supporting the expandable shell is clipped onto the thyroid cartilage and in other embodiments of the invention the support means is passed through the thyroid cartilage.

In some embodiments of the invention the actuating means for locating a paralyzed vocal cord in a predetermined phonation position is a movable rigid member. In another embodiment of the invention the actuating means is a bellows that expands upon the movement of an internal piston member. In a further embodiment of the invention the actuating means is a movable ratchet member.

A combination pump and reservoir member can be incorporated in selected embodiments of the invention to replace the septum and/or operate in tandem with the septum. The pump/ reservoir member includes a valve that is normally closed but opens upon infusion of fluid or pumping of fluid past the reservoir space. Fluid can be received back into the reservoir upon deforming the valve. Thus fluid can flow bi-directionally to adjust the position of the actuating means to change the location of the paralyzed vocal cord after surgical installation of the prosthetic device is completed. The relocation of a paralyzed vocal cord in an optimum phonation position can thus be accomplished following surgery. Other desired changes in the phonation position of a paralyzed vocal cord can also be accomplished post surgically as desired.

The invention accordingly comprises the constructions and method hereinafter described, the scope of the invention being indicated in the claims.

DESCRIPTION OF THE DRAWINGS

In the accompanying drawings,

FIG. 1 is a simplified schematic perspective view of a prosthetic device for a paralyzed vocal cord incorporating one embodiment of the invention;

FIG. 2 is a simplified schematic view thereof during affixation to the thyroid cartilage;

FIG. 3 is a simplified schematic perspective view thereof after being folded for affixation to the thyroid cartilage;

FIG. 4 is an enlarged side view thereof, partly shown in section, after affixation to the thyroid cartilage with the actuator in an unexpanded condition;

FIG. 5 is a side view thereof similar to FIG. 4 with the actuator in an expanded condition;

FIG. 8 is a simplified schematic perspective view of another embodiment of the invention;

FIG. 9 is a simplified schematic view thereof after affixation to the thyroid cartilage;

FIG. 10 is an enlarged side view thereof, partly shown in section, and affixed to the thyroid cartilage;

FIG. 11 is a simplified schematic perspective view of another embodiment of the invention;

FIG. 12 is a simplified schematic view thereof after affixation to the thyroid cartilage;

FIG. 13 is a simplified schematic anatomical view of the larynx showing a top plan view of the prosthetic device, partly in section, in an implanted position on the thyroid cartilage;

FIG. 14 is a simplified schematic perspective view of yet another embodiment of the invention;

FIG. 15 is a simplified schematic anatomical view of the larynx showing a top plan view of the prosthetic device, partly in section, in an implanted position on the thyroid cartilage and prior to expansion of the actuator;

FIG. 16 is a top plan view thereof similar to FIG. 15 after expansion of the actuator;

FIG. 17 is a simplified schematic perspective view of another embodiment of the invention in an implanted condition;

FIG. 18 is an enlarged side view thereof partly shown in section, and affixed to the thyroid cartilage;

FIG. 21 is a sectional view of another embodiment of the invention in an implanted condition;

FIG. 22 is a sectional view of still another embodiment of the invention in an implanted condition;

FIGS. 23 and 24 are sectional views of septums which can be incorporated in any of the embodiments of the invention; and, FIG. 25 is a sectional view of a reservoir pump and valve arrangement which can be incorporated in selected embodiments of the invention.

Corresponding reference characters indicate corresponding parts throughout the several views of the drawings.

DETAILED DESCRIPTION OF THE INVENTION

Figure 6:
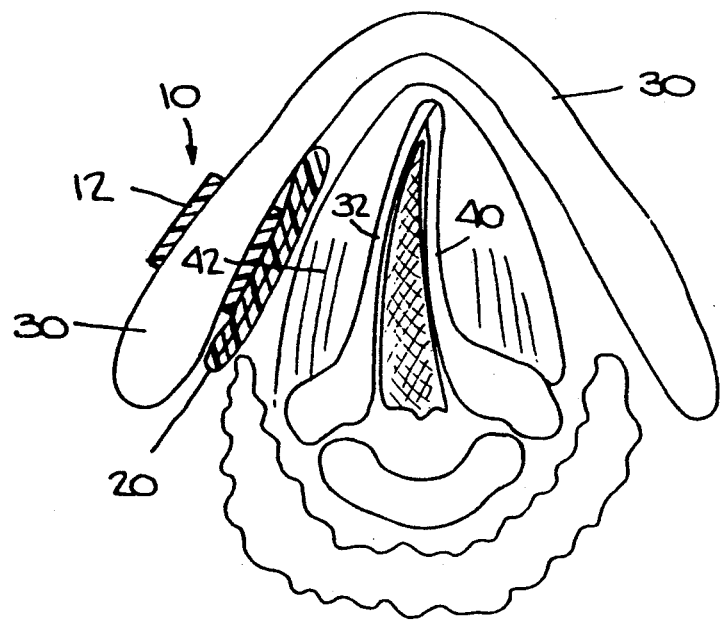
FIG. 6 is a simplified schematic anatomical view of the larynx showing a top plan view of the prosthetic device, partly in section, in an implanted position on the thyroid cartilage prior to expansion of the actuator.

An adjustable prosthetic device for positioning of paralyzed vocal cords incorporating one embodiment of the invention is generally indicated by the reference number 10 in FIG. 1.

The prosthetic device 10 includes a clip member 12 having an elbow 14. The clip 12, which can be formed of titanium, supports a tube 16 which can be formed of silicone. The tube 16 is provided with a septum 18 at one end portion thereof and with a hollow expandable shell portion 20 at an opposite end thereof. The septum 18 and the shell portion 20 are supported on the clip 12 in any suitable known manner. A fluid flow path 22 thus extends in the tube 16 from a chamber 24 in the septum 18 to a chamber 26 in the expandable shell 20 (FIGS. 4 and 5). A tail portion 28 of the clip member 12 extends beyond the expandable shell 20.

Figure 7:
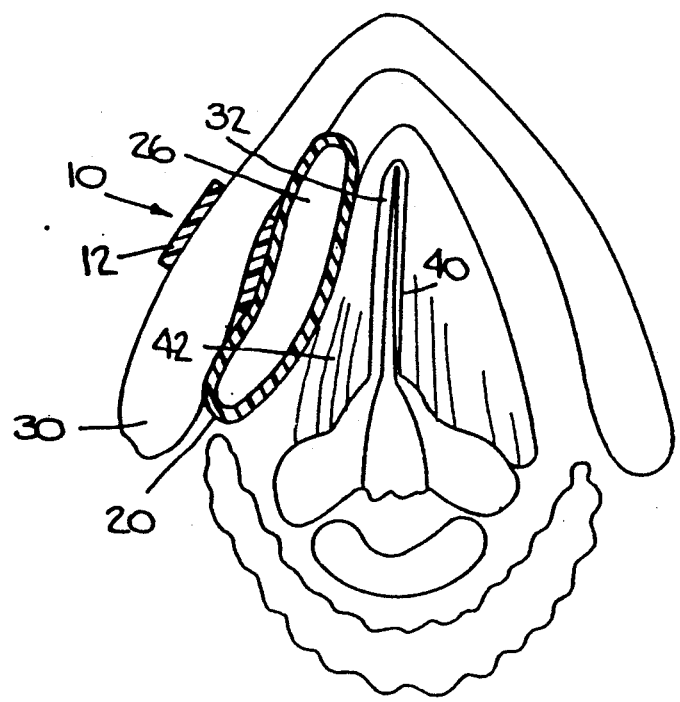
FIG. 7 is a top plan view thereof, similar to FIG. 6, with the actuator in an expanded condition.
Figure 19:
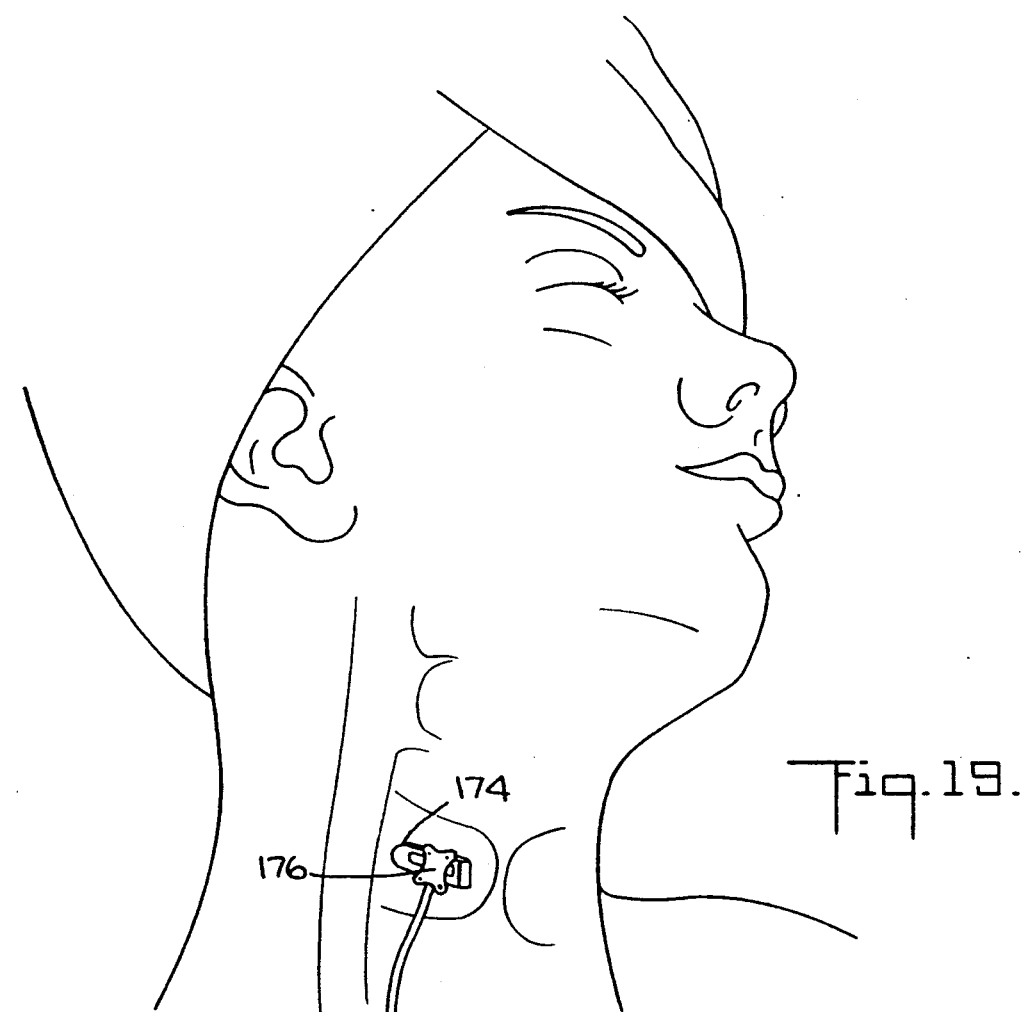
FIG. 19 is a simplified schematic perspective view of yet another embodiment of the invention in an implanted condition.

The prosthetic device 10 is supported on a thyroid cartilage 30 proximate a paralyzed vocal cord 32 (FIGS. 6 and 7). Thus the elbow portion 14 of the device 10 is shaped to conform around an upper edge portion 34 of the cartilage 30 and the tail end portion 28 of the clip member 12 is bent around a lower edge 36 of the cartilage 30, thereby anchoring the device 10 to the cartilage 30. Under this arrangement the hollow expandable shell 20 is disposed between the cartilage 30 and the muscle 42 of the paralyzed vocal cord 32 (FIGS. 6 and 7). The septum 18 is thus on the outside of the thyroid cartilage 30 and is accessible through the skin of the neck (not shown) by an infusion needle 38 as shown in FIGS. 4 and 5. If desired, the elbow portion 14 can be extended below the septum 18 as indicated at 15 in FIG. 4. The extension 15 and the tail end portion 28 can then be perforated and fastened to the thyroid cartilage 30 by screws 17 and 19.

During installation of the prosthetic device 10, the septum 18, the tube 16 and the hollow expandable shell 20 are substantially free of fluid, and the shell 20 is in a substantially flattened condition as most clearly shown in FIG. 4.

After the device 10 has been installed on the thyroid cartilage 30, the infusion needle 38 is directed toward the septum 18 and a predetermined amount of fluid (not shown) such as saline is infused into the septum for passage through the tube 16 into the hollow expandable shell 20.

It will be noted that the septum 18 is shown in simplified schematic form and is of the type which includes known leak-resistant properties that enable the septum to maintain a leak-tight condition when the infusion needle 38 is withdrawn from the septum 16.

For example, a known septum 50 as shown in FIG. 23 is a more detailed version of the septum 18 and includes a known self-sealing member 52, and a needle stop member 54 defining a septum chamber 56. A jacket member 58 surrounds the needle stop member 54 and can be supported on the clip 12. The tube 16 communicates with the septum chamber 56. The septum 50 can thus replace the septum 18.

Referring to FIGS. 4 and 5, the septum chamber 24, the fluid flow path 22 and the shell chamber 26, which are all communicable, constitute a closed system that is expandable only at the area of the shell 20. Thus the amount of expansion of the shell 20 corresponds to predetermined amounts of fluid injected into the septum 16 which cause expansion of the shell 20.

Fluid expansion of the shell 20 will cause the paralyzed vocal cord 32 to move from a receded divergent position as shown in FIG. 6, to a convergent phonation position shown in FIG. 7 wherein the vocal cord 32 is converged with a non-paralyzed vocal cord 40. A relocation of the paralyzed vocal cord 32 in the phonation position is based on the amount of fluid injected into the closed system of the device 10.

The phonation position of the paralyzed vocal cord 32 established by the expandable shell 20 can be empirically determined by the surgeon and patient during surgery. However after surgery is completed and the vocal cord anatomy is no longer directly accessible by the surgeon, the prosthetic device 10 can be post-operatively adjusted to change the phonation position of the paralyzed vocal cord to afford the patient optimal voice quality and breathing function.

In order to make a further adjustment of the phonation position of the paralyzed vocal cord 36, fluid can either be added or removed from the closed system of the prosthetic device 10 via the infusion needle 38 without the need for further surgery. The addition or removal of fluid from the closed system will expand or contract the shell 20 and thus move the paralyzed vocal cord 32 to a desired position.

If the vocal cord 32 is temporarily paralyzed and it is desired to restore the preoperative condition of the vocal cord, this can be accomplished by evacuating the closed system of the prosthetic device 10 to place the shell 20 in its deflated condition as shown in FIG. 6. If desired, the device 10 can be surgically removed should the need arise.

Although the size of the device 10 can be varied in accordance with the particular needs of the patient, some dimensional magnitudes of the device 10 are exemplified as follows. The projection of the expandable shell 20 from the cartilage 30 when the shell 20 is in its collapsed condition is approximately 1.0 to 3.0 mm. The projection of the expandable shell 20 from the cartilage 30 when the shell is inflated to place the vocal cord 32 in a compromise phonation position is approximately 3.0 to 12.0 mm.

The nominal overhang of the septum 16 from the top edge 34 of the cartilage 30 is approximately 6.0 to 16.0 mm. and the tail end portion 28 of the clip member extends approximately 6.0 to 8.0 mm. from the lower edge portion 36 of the cartilage 30. The height of the expandable shell 20 (FIG. 5) is approximately 5.0 to 8.0 mm. and the horizontal length of the shell 20 (FIG. 1) is approximately 15.0 mm.

Another embodiment of the prosthetic device is generally indicated by the reference number 60 in FIGS. 8-10. Referring to FIG. 8, the prosthetic device 60 comprises a hollow U-shaped clip member 62 with leg portions 64 and 66. A tube member 68, provided on the clip member 62 has a septum 70 at one end of the tube and an expandable shell 72 at an opposite end of the tube. The septum 70 and the expandable shell 72, which are supported on the respective legs 64 and 66, are similar to the septum 18 and the expandable shell 20 of the prosthetic device 10.

A fluid flow path 74 (FIG. 10) in the tube member 68 communicates with a septum chamber 76 and a shell chamber 78 to define a closed inner space of the prosthetic device 60.

The leg portions 64 and 66 of the clip member 62 are biased to converge toward each other and are maintained in a divergent relationship by means of a spacer screw 80 (FIG. 10) that passes through the leg portion 64 and bears against the leg portion 66. The tube member 68 on the leg portion 64 bypasses the screw 80. Securement prongs 82 are provided on the leg 64 directed toward the leg 66.

The prosthetic device 60 is installed on the thyroid cartilage 30 in the manner shown in FIGS. 9 and 10 wherein the leg portions 64 and 66 of the clip member 62 straddle the thyroid cartilage 30. When the expandable shell 72 is positioned at a desired elevation on the thyroid cartilage 30, the spacer screw 80 is driven outwardly of the leg portion 64 in the direction of the arrow 84 (FIG. 10) to permit the leg portions 64 and 66 to converge and grip the thyroid cartilage 30. The securement prongs 82 penetrate the thyroid cartilage 30 to further anchor. The device 60 to the cartilage 30 and prevent slippage of the shell 72 from its desired elevation.

The prosthetic device 60 is infused with fluid in a manner similar to that previously described for the device 10 to expand the shell 72 and thus move a paralyzed vocal cord, such as the vocal cord 32 (FIG. 7), to a predetermined phonation position.

Another embodiment of the prosthetic device is generally indicated by the reference number 90 in FIG. 11. The prosthetic device 90 comprises a U-shaped clip member 92 having leg portions 94 and 96 biased to converge toward each other. A tube member 98 provided on the clip member 92 has a septum 100 at one end of the tube, and an expandable shell 102 at an opposite end of the tube respectively similar to the septum 70 and the expandable shell 72 of the device 60. Securement prongs 104 are provided on the leg 94 directed toward the leg 96. The device 90 as thus described is similar to the device 60, but omits the spacer screw 80.

A lip 106 is formed on the leg 94 for engagement by a tool (not shown) having a hook-like end that is receivable in the lip 106 to exert a holding force on the leg 94 to pull the leg 94 away from the leg 96.

The prosthetic device 90 is installed onto the thyroid cartilage 30 in the manner shown in FIGS. 12 and 13 wherein an elbow portion 108 of the clip member 92 engages the upper edge portion 34 of the thyroid cartilage 30. The leg portion 94 is then released by the hooked tool (not shown) to permit the legs 94 and 96 to converge toward each other and grip the thyroid cartilage 30 therebetween, to affix the position of the prosthetic device 90 on the thyroid cartilage 30.

The expandable shell 102 is thus positioned proximate a paralyzed vocal cord 110 (FIG. 13). Infusion of fluid into the septum 100 to expand the shell 102 moves the paralyzed vocal cord 110 to a predetermined phonation position, which can be later adjusted by further infusions of fluid or withdrawal of fluid as required by the particular needs of the patient.

Another embodiment of the prosthetic device is generally indicated by the reference number 120 in FIG. 14. The prosthetic device 120 includes a hollow tubular portion 122 which, at one end, is fed by a septum 124, and at an opposite end, feeds an expandable shell 126. The septum 126 is shown in simplified schematic form and can be of the type indicated by reference number 50 in FIG. 23. The septum 50 can be adapted to replace the septum 124 by omitting the tube 16 and joining the tube 122 to the base of the needle stop member 54 (FIG. 23) to communicate with the chamber 56.

The prosthetic device 120 is affixed to the thyroid cartilage 30 through an opening 128 that is surgically provided in any suitable known manner. The expandable shell 126 is thus disposed proximate the paralyzed vocal cord 110 and the septum 124 is disposed on the outer portion of the thyroid cartilage 30 to permit access by an infusion needle 38 as shown in FIG. 16.

A chamber 130 of the expandable shell 126 can thus be expanded a predetermined amount to enable the shell 126 to move the paralyzed vocal cord 110 to a predetermined phonation position as shown in FIG. 16. Post-operative adjustments of the amount of shell expansion can be made by adding or withdrawing fluid from the shell 126 via the septum 124.

Still another embodiment of the invention is generally indicated by the reference number 140 in FIG. 18. The prosthetic device 140 includes a J-shaped clip member 42 having a short leg portion 144 and a long leg portion 46. A flexible tubular member 148 is provided on the clip member 142 and includes a hollow expandable shell 150 at one end of the tube and supported on the leg 146. The tube 148 includes an elongated unsupported portion 152 that extends away from the short leg 144 and has a known septum 154 provided at the opposite tube end. The septum 154 includes a needle-penetrable self sealing member 156, a needle stop member 158 and a jacket 160. The septum 154 is communicable with the expandable shell 150 through the tube 148.

The clip member 142 is installed on the thyroid cartilage 30 as shown in FIG. 18, such that an elbow portion 62 of the clip member 142 engages the top edge portion 34 of the thyroid cartilage 30 which is sandwiched between the leg portions 144 and 146. If desired, the leg portions 144 and 146 can be normally biased to converge toward each other to grip the cartilage 30 when the clip member 142 is positioned thereon. They can also be fixed to the cartilage in the manner already described for the device 10 at FIG. 4.

The expandable shell 150 is thus disposed proximate a paralyzed vocal cord such as the vocal cord 32 of FIG. 7.

The space 164 within the septum 154, the fluid flow passage 166 within the tubular member 148, and the space 168 within the expandable shell 150 define a closed interior space for fluid within the prosthetic device 140. Thus the infusion of fluid into the closed interior space of the prosthetic device 140 via the septum 154 allows the expandable shell 150 to expand from a deflated condition (not shown) to an expanded condition as shown in FIG. 18. Under this arrangement, fluidic expansion of the shell 150 operates to move the paralyzed vocal cord to a desired phonation position.

Provision of the elongated unsupported tubular portion 152 permits the septum 154 to be located away from the thyroid cartilage 30, as for example, at the base of the neck. As in all previously disclosed embodiments, the device 140 is post-operatively adjustable to change the phonation position of the paralyzed vocal cord.

Figure 20:
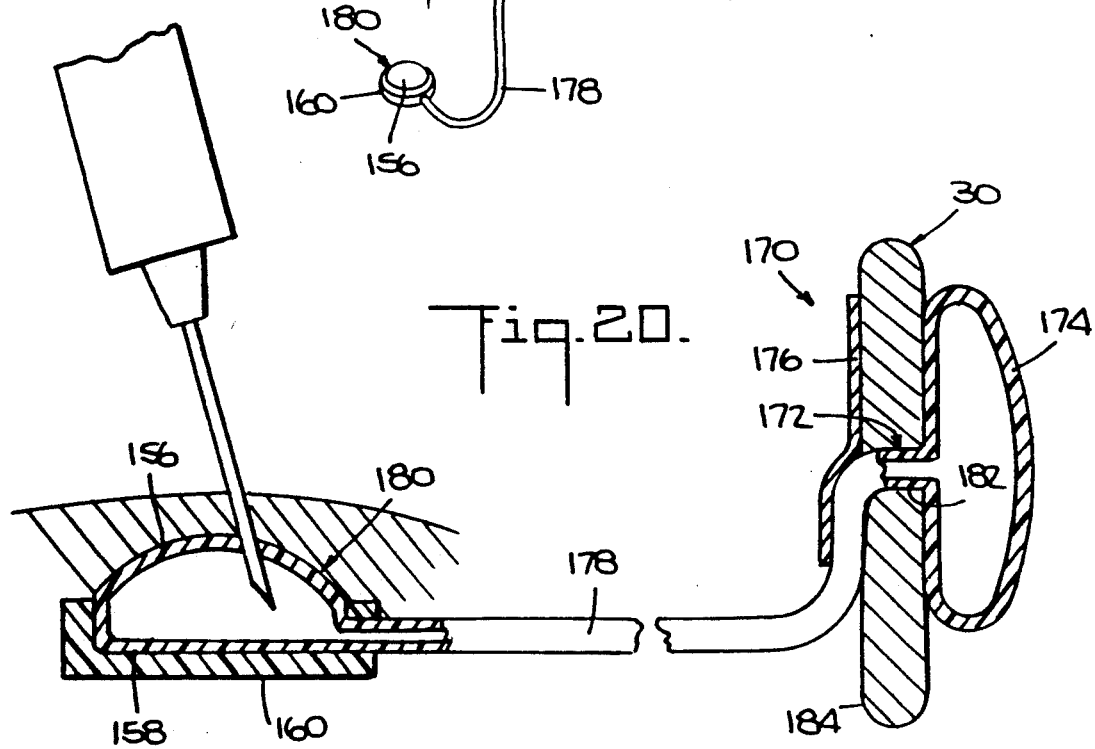
FIG. 20 is an enlarged sectional view thereof affixed to the thyroid cartilage.

Still another embodiment of the invention is generally indicated by the reference number 170 in FIG. 20. The prosthetic device 170 includes a tubular member 172 with an expandable shell 174 provided at one end thereof. The tubular member 172 bends at the outside 184 of the thyroid cartilage 30 and extends along a substantially rigid platelike gripper member 176. The thyroid cartilage 30 is thus sandwiched between the gripper member 176 and the shell 174 as shown in FIG. 20. The gripper and shell members may be further fixed in place with screws or biologically acceptable adhesives. The tubular member 172 includes a flexible elongated unsupported portion 178 that extends away from the gripper member 176 and has a septum 180 identical to the septum 154 provided at the opposite tube end. The septum 180 is communicable with the expandable shell 174 through the tubular member 172 in a manner similar to that described for the device 140.

The device 170 is installed in the thyroid cartilage 30 through a surgically formed opening 182 such that the expandable shell 174 is proximate a paralyzed vocal cord such as the vocal cord 32 (FIG. 7). Infusion of fluid into the septum 180 by the needle 38 as shown in FIG. 20, enables the expandable shell 174 to expand in the manner previously described for the prosthetic device 140.

It should be noted that the type of septum used with the prosthetic device for a vocal cord is structured according to the location of the septum. Depending upon the needs of the patient, and the feasibility of locating a septum at a location remote from the thyroid cartilage, the septum can be structured to blend in with the anatomical features of the patient. For example, a septum 190 as shown in FIG. 24 includes a generally conical shaped needle stop member 192 and a correspondingly shaped jacket (not shown) for the needle stop member. The septum 190 also includes a needle penetrable self-sealing member 194 engagable by a needle 38. A tubular member 196 extending from the septum 190 communicates with an expandable shell (not shown) of a prosthetic device for a vocal cord of the type previously disclosed herein. The location of the septum 190, for example, can be along the side of the neck if desired.

Another embodiment of a prosthetic device for a vocal cord is generally indicated by the reference number 200 in FIG. 21. The device 200 includes a tubular member 202 that communicates with a piston member 204 having a head portion 214 disposed within an expandable bellows 206 that is located on one side of the thyroid cartilage 30 proximate a paralyzed vocal cord (not shown). A gripper member 208 is provided on the outside of the thyroid cartilage 30 such that the thyroid cartilage 30 is sandwiched between the bellows 206 and the gripper member 208.

The tubular member 202 communicates with a septum of the type previously disclosed herein. Thus fluid infused into the septum will engage a stem portion 210 of the piston 204 to urge the piston head 214 to move away from the thyroid cartilage 30 thus expanding the bellows 206. The consequential expansion of the bellows 206 operates to move a paralyzed vocal cord to a desired phonation position. The device 200 is installed in the thyroid cartilage 30 in a surgically formed opening 212.

The bellows 206 is thus adjustable during the surgical installation and is also postoperatively adjustable to optimize the phonation position of the paralyzed vocal cord.

A further embodiment of a prosthetic device for a paralyzed vocal cord is generally indicated by the reference number 220 in FIG. 22. The prosthetic device 220 includes a support member 222 disposed in a surgically formed opening 224 of the thyroid cartilage 30. The support member 222 includes gripper flanges 226 and 228 disposed at opposite sides of the thyroid cartilage 30. A ratchet member 232 supported by the support member 222 includes a head portion 234 and a stem portion 236 extending from the head portion 234. The stem portion 236 has radially projecting ratchet-like formations 240 engagable against an inner wall 242 of the support member 222.

The device 220 is installed in the thyroid cartilage 30 such that the head portion 234 of the ratchet member 232 is proximate a paralyzed vocal cord (not shown). Movement of the head portion 232 is accomplished by infusing fluid into the tubular member 244 via the septum (not shown) to bear against the stem portion 236 and urge the stem portion to move relative to the support member 222. Thus infusion of fluid into the device 220 causes the head portion 234 to move a paralyzed vocal cord to a desired phonation position.

The device 220 is a uni-directionally adjustable device which can be protracted with respect to the support member 228 but is not retractable by fluid movement therein. However the device 220 is postoperatively adjustable to obtain a desired protracted position of the head portion 234 which will correspond to an optimum phonation position of a paralyzed vocal cord.

In some instances it may be desirable to pump fluid to the expandable shell rather than input a direct infusion of fluid to the expandable shell. A pumping arrangement is generally indicated by the reference number 250 in FIG. 25. The pumping arrangement 250 includes a combination pump and reservoir 252, having a generally bulbous shape, which can be filled with fluid via a tube member 254 in any suitable known manner as through a septum such as the septum 50 shown in FIG. 23. A valve assembly 256 is provided at an output end 258 of the reservoir 252. The valve assembly 256 includes a ball valve 260 normally in a closed position on a valve seat 262 under the influence of a biasing spring 264. One or more outlet ports 266 of the valve assembly 256 communicate with a tubular member 268 that leads to an expandable shell (not shown) such as the shell 150, 174, or the piston member 204 or the ratchet member 232, for example. The valve assembly 256 further includes a valve sleeve 270. The pump and reservoir 252 is formed of a flexible biocompatible material such as silicone, as are the other components of the valve assembly 256 such as the valve seat 262 and the valve sleeve 270.

The pumping arrangement 250 is implanted percutaneously and a supply of fluid is provided in the reservoir chamber 272 in any suitable known manner. Thus upon palpating the pump and reservoir 252, fluid within the chamber 272 exerts a pressure against the ball valve 260 to unseat the valve from the valve seat 262 and cause fluid to flow through the outlet port 266 into the tube 268 and into the shell 150 of FIG. 18, for example. The expandable shell 150 is thus expandable based on palpation of the pump and reservoir 252 rather than upon infusion of fluid into the septum 154 (FIG. 18). Such palpation can be manually accomplished by a physician or the individual with the prosthesis.

Under this arrangement the expandable shell 150 is postoperatively adjustable by palpation of the pump and reservoir 252. If it is desired to decrease the expansion of the shell 150 the valve sleeve 270 is gripped and distorted to unseat the ball 260 from the valve seat and thus enable fluid to flow from the tube 268 back into the valve chamber 272. Thus by appropriately adding or removing fluid from the expandable shell 150, an optimum phonation position of a paralyzed vocal cord can be obtained corresponding to a desired expansion of the expandable shell 150.

The pumping arrangement 250 can be adapted to other embodiments disclosed herein such as the device 170 of FIG. 20, the device 200 of FIG. 21 and the device 220 of FIG. 22, for example.

If desired, the reservoir chamber 272 can be omitted entirely such that fluid is infused through the tube member 254 directly to the valve 256 from a septum such as the septum 50. The pressure of the fluid infusion is predetermined to enable the ball valve 260 to unseat from the valve seat 262. When it is desired to remove fluid, the valve sleeve 270 is distorted to unseat the ball valve 260 and enable fluid to be withdrawn from the septum by a needle 38.

It should be noted that a preferred fluid for incorporation in the prosthetic device is isotonic saline. However other materials may also be feasible such as an electrorheological polymer which has a low viscosity comparable to water in its natural state. When an electrical charge is applied, the polymer will gel and remain so until the charge is removed. In addition, a pH sensitive polymer can also be used consisting of two parts, both of which have low viscosities. When the components are mixed, the pH of the individual components is altered and the material gels. A further possible fluid medium is a thixotropic gel which flows when stressed as when passed through a needle. When the gel is in an unstressed condition it assumes a gel-like state.

The use of gel materials as opposed to saline is to resist deformation of an expandable shell due to stresses imposed by the body during the healing process. A gel has been found to resist the body's forces to a greater degree than saline.

Some advantages of the invention evident from the foregoing description include a prosthetic device that locates a paralyzed vocal cord in a predetermined phonation position and includes actuating means for adjusting and changing the location of the paralyzed vocal cord. A further advantage is that the actuating means are accessible via fluid actuation to provide fluid expansion of a shell, mechanical expansion of a bellows via a piston, or displacement of a physical locating device such as the head portion of a ratchet member.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A prosthetic device for treating vocal cord paralysis comprising,
    a) movable actuating means for locating a paralyzed vocal cord in a first predetermined phonation position, said actuating means having a free contact surface adapted to contact said paralyzed vocal cord to move said paralyzed vocal cord to said first predetermined phonation position,
    b) support means adapted to support said actuating means on a thyroid cartilage proximate the paralyzed vocal cord, and
    c) a fluid receiving station for inputting fluid to the actuating means to adjust the movement of the actuating means to change the location of the paralyzed vocal cord from said first predetermined phonation position to another selected position.

2. The prosthetic device as claimed in claim 1 wherein the fluid receiving station includes means for permitting infusion and withdrawal of fluid.

3. The prosthetic device as claimed in claim 1 wherein said actuating mans include a flexible expandable shell member having a fluid receiving chamber, said shell being communicable with said fluid receiving station and projectable from said support means by predetermined amounts corresponding to the amount of fluid in said chamber such that expansion of said shell actuates movement of said paralyzed vocal cord.

4. The prosthetic device as claimed in claim 1 wherein said actuating means comprise an expandable bellows.

5. The prosthetic device as claimed in claim 4 wherein said bellows include an internal piston member communicable with said fluid receiving station such that fluid pressures imposed on said piston member cause expansion of said bellows away from said support means.

6. The prosthetic device as claimed in claim 1 wherein said actuating means include a ratchet member communicable with said fluid receiving station, said ratchet member having a head portion protractable from said support member such that fluid pressure imposed on said ratchet member causes protraction of said head portion away from said support member.

7. The prosthetic device as claimed in claim 1 wherein said support means comprise a clip member having an elbow portion engagable with an edge portion of said thyroid cartilage.

8. The prosthetic device as claimed in claim 7 wherein said clip member is U-shaped and has a pair of leg portions biased to converge toward each other to grip said thyroid cartilage.

9. The prosthetic device as claimed in claim 8 wherein one of said leg portions include a prong directed toward the other said leg portion.

10. The prosthetic device as claimed in claim 8 wherein said clip member includes spacer means for maintaining said leg portions in a predetermined divergent position.

11. The prosthetic device as claimed in claim 10 wherein said spacer means include a screw member threaded into one of said leg portions for engagement with the other leg portion.

12. The prosthetic device as claimed in claim 8 wherein said clip member includes tool engagement means for engagement with a spacer tool to diverge said leg portions.

13. The prosthetic device as claimed in claim 7 wherein a tube member is provided on said clip member, said movable actuating means being at one end portion of said tube member and said fluid receiving station being at an opposite end portion of said tube member such that said actuating means is communicable with said fluid receiving station through said tube member.

14. The prosthetic device as claimed in claim 13 wherein said actuating means include a flexible expandable shell member having a fluid receiving chamber, said shell being communicable with said fluid receiving station and projectable from said support means by predetermined amounts corresponding to the amount of fluid in said chamber such that expansion of said shell actuates movement of said paralyzed vocal cord.

15. The prosthetic device as claimed in claim 13 wherein said clip member is U-shaped and has a pair of leg portions, said actuating means being provided at one of the leg portions.

16. The prosthetic device as claimed in claim 15 wherein said fluid receiving station comprises a septum.

17. The prosthetic device as claimed in claim 16 wherein said septum is provided at the other said leg portion.

18. The prosthetic device as claimed in claim 16 wherein said septum is located remote from said leg portion and away from said support means.

19. The prosthetic device as claimed in claim 15 wherein said fluid receiving station is a manually operable pumping device.

20. The prosthetic device as claimed in claim 19 wherein said pumping device includes a normally closed valve that is deformable into an open condition.

21. The prosthetic device as claimed in claim 1 wherein said support means comprise a tube, said actuating means being provided at one end of said tube.

22. The prosthetic device as claimed in claim 21 wherein said actuating means include a flexible expandable shell member having a fluid receiving chamber, said shell being communicable with said fluid receiving station and projectable from said support means by predetermined amounts corresponding to the amount of fluid in said chamber such that expansion of said shell actuates movement of said paralyzed vocal cord.

23. The prosthetic device as claimed in claim 21 wherein said actuating means comprise an expandable bellows.

24. The prosthetic device as claimed in claim 23 wherein said bellows include an internal piston member communicable with said fluid receiving station such that fluid pressure imposed on said piston member cause expansion of said bellows away from said support means.

25. The prosthetic device as claimed in claim 21 wherein said actuating means include a ratchet member communicable with said fluid receiving station, said ratchet member having a head portion protractable from said support member such that fluid pressure imposed on said ratchet member causes protraction of said head portion away from said support member.

26. The prosthetic device as claimed in claim 21 wherein said fluid receiving station is provided at an opposite end of said tube.

27. The prosthetic device as claimed in claim 26 wherein said actuating means and said fluid receiving station are spaced a predetermined amount from each other to sandwich a thyroid cartilage therebetween.

28. The prosthetic device as claimed in claim 27 wherein said fluid receiving station comprises a septum.

29. The prosthetic device as claimed in claim 26 wherein said tube includes an elongated portion extending away from said actuating means to a location remote from said actuating means.

30. The prosthetic device as claimed in claim 29 wherein said fluid receiving station comprises a septum.

31. A method of restoring and improving phonation in an individual having a paralyzed vocal cord and a functional vocal cord comprising,
   a) supporting an actuator proximate the paralyzed vocal cord for movement between the paralyzed vocal cord and the thyroid cartilage,
   b) moving the actuator member away from the thyroid cartilage toward the paralyzed vocal cord to move the paralyzed vocal cord in a direction toward the functional vocal cord to a first predetermined phonation position, and
   c) obtaining movement of the actuator member by inputting fluid to the actuator member such that the actuator member is movable by an amount that corresponds to the amount of fluid inputted to the actuator member.

32. The method of claim 31 including postoperatively adjusting the first predetermined phonation position of the paralyzed vocal cord by changing the amount of fluid inputted to the actuator member to move the actuator member from an actuator position that corresponds to the first predetermined phonation position to another selected actuator position that corresponds to another selected phonation position of the paralyzed vocal cord.

33. The method of claim 31 wherein the movement of the actuator member is accomplished by fluid expansion of the actuator member.

34. The method of claim 31 wherein movement of the actuator member is accomplished by piston actuated movement of the actuator member.

35. The method of claim 31 wherein movement of the actuator member is accomplished by displacement of the actuator member to a selected position corresponding to the first predetermined phonation position.

36. The method of claim 31 including obtaining reversible movement of the actuator member.

* * * * *

UNITED STATES PATENT AND TRADEMARK OFFICE
CERTIFICATE OF CORRECTION

PATENT NO. : 5,197,982

DATED : March 30, 1993

INVENTOR(S) : Manning M. GOLDSMITH, III and Bruce W. PEARSON

It is certified that error appears in the above-identified patent and that said Letters Patent is hereby corrected as shown below:

At column 6, line 41, change "8-10.10." to --8-10.--.

At column 7, line 4, change "anchor. The" to --anchor the--.

At column 8, line 4, change "42" to --142--.

At column 8, line 5, change "46" to --146--.

At column 8, line 17, change "62" to --162--.

Signed and Sealed this

Fourteenth Day of December, 1993

Attest:

BRUCE LEHMAN

Attesting Officer        Commissioner of Patents and Trademarks